(12) United States Patent
Yu et al.

(10) Patent No.: US 9,988,355 B2
(45) Date of Patent: Jun. 5, 2018

(54) FORM A OF MESYLATE FOR NICOTINAMIDE DERIVATIVES AND PREPARATION METHOD AND APPLICATION THEREOF

(71) Applicant: SHANGHAI SUNTRONG BIOTECHNOLOGY CO., LTD., Shanghai (CN)

(72) Inventors: Yinglu Yu, Shanghai (CN); Jinyao Chen, Shanghai (CN); Dongxu Yi, Shanghai (CN)

(73) Assignee: SHANGHAI SUNTRONG BIOTECHNOLOGY CO., LTD., Shanghai (CN)

( * ) Notice: Subject to any disclaimer, the term of this patent is extended or adjusted under 35 U.S.C. 154(b) by 0 days. days.

(21) Appl. No.: 15/324,221

(22) PCT Filed: Jul. 8, 2015

(86) PCT No.: PCT/CN2015/083572
§ 371 (c)(1),
(2) Date: Jan. 5, 2017

(87) PCT Pub. No.: WO2016/004873
PCT Pub. Date: Jan. 14, 2016

(65) Prior Publication Data
US 2017/0183310 A1    Jun. 29, 2017

(30) Foreign Application Priority Data
Jul. 8, 2014  (CN) .......................... 2014 1 0323412

(51) Int. Cl.
C07D 401/12 (2006.01)
A61K 31/44 (2006.01)
C07D 213/82 (2006.01)
C07C 309/04 (2006.01)
C07D 213/803 (2006.01)

(52) U.S. Cl.
CPC .......... C07D 213/82 (2013.01); C07C 309/04 (2013.01); C07D 213/803 (2013.01); *C07B 2200/13* (2013.01)

(58) Field of Classification Search
None
See application file for complete search history.

(56) References Cited

U.S. PATENT DOCUMENTS

2011/0184023 A1* 7/2011 Yuan .................... C07D 213/82
514/332

* cited by examiner

*Primary Examiner* — Zinna Northington Davis
(74) *Attorney, Agent, or Firm* — Kile Park Reed & Houtteman PLLC

(57) ABSTRACT

The invention discloses a form A of mesylate for nicotinamide derivatives and preparation method and application thereof, wherein the XRPD pattern of the form A of mesylate for nicotinamide derivatives has a diffraction peak at $2\theta$=5.34, 10.341, 14.438, 15.841, 17.32, 18.301, 18.68, 19.005, 19.577, 20.26, 21.161, 21.859, 22.379, 23.04, 23.5, 24.177, 24.959, 25.881, 26.641, 27.18, 28.3, 28.999, 29.501, 31.96, 32.258, 33.999, 36.798, 37.38 and 41.297 with the error range of the $2\theta$ values being ±0.2. The form A of mesylate for nicotinamide derivatives provided by the present invention has excellent high-temperature stability, high-humidity stability and illumination stability, and it can be applied to drugs for treating advanced non-small cell lung cancers, gastric cancers, liver cancer or breast cancer. It has preferable bioavailability, and meanwhile the provided qualitative and quantitative information has great significance on further study of the efficacy of such solid drugs.

15 Claims, 5 Drawing Sheets

FORM A OF MESYLATE FOR NICOTINAMIDE DERIVATIVES AND PREPARATION METHOD AND APPLICATION THEREOF

TECHNICAL FIELD

The present invention relates to a molecular targeted antitumor drug, in particular to a form A of mesylate for nicotinamide derivatives, which is named Form A, and preparation method and application thereof.

BACKGROUND ART

Nicotinamide derivative (Aptinib), with a molecular formula being $C_{24}H_{23}N_5O$ and a chemical name of N-[4-(1-cyanocyclopentyl) phenyl]-2-(4-pyridylmethyl) amidogen-3-pyridineethanamine, is a molecularly targeted antitumor drug and is a typical small molecule vascular endothelial growth factor tyrosine kinase inhibitor that can be used to treat advanced non-small cell lung cancer, gastric cancer, liver cancer, breast cancer and the like. The Chinese invention patent CN101676267 discloses the preparation method and application of the nicotinamide derivatives mesylate (with molecular formula $C_{24}H_{23}N_5O.CH_4O_3S$). The nicotinamide derivative mesylate (hereinafter referred to as "nicotinamide derivative mesylate solids with needle shape") obtained according to the method described in CN 101676267 is an anhydrate, which has needle shape and of hygroscopicity. As is known to those skilled in the art, a highly hygroscopic solid is difficult to be made into formulations under pharmaceutical processing conditions, whereas solids with needle shape are very viscous and of poor flowability due to the large amount of static electricity. Accordingly, there is a need for a crystal form of the nicotinamide derivative mesylate with superior physicochemical properties, which can be advantageously used in pharmaceutical processing and pharmaceutical compositions.

As we all know, the stability and bioavailability of different crystal forms of the same drug may be significantly different, thus affecting the efficacy of drug. Therefore, it is of great significance to develop new crystal forms of nicotinamide derivatives which are more advantageous to use in drug processing and pharmaceutical compositions, and to provide more qualitative and quantitative information for therapeutic effect studies of solid drug.

SUMMARY OF THE INVENTION

The problem to be solved by the present invention is that the shape and hygroscopicity of the existing nicotinamide derivative mesylate are disadvantageous for pharmaceutical processing and use in pharmaceutical compositions, to develop new crystal forms of nicotinamide derivatives mesylate, which provide more questions on qualitative and quantitative information on the therapeutic effect studies of solid drug.

In order to solve the above technical problem, the technical solution adopted in the present invention is to provide a form A of mesylate for nicotinamide derivatives with characteristic peak in the X-ray powder diffracogram at 2θ values of 5.34, 10.341, 14.438, 15.841, 17.32, 18.301, 18.68, 19.005, 19.577, 20.26, 21.161, 21.859, 22.379, 23.04, 23.5, 24.177, 24.959, 25.881, 26.641, 27.18, 28.3, 28.999, 29.501, 31.96, 32.258, 33.999, 36.798, 37.38, 41.297 respectively with the error range of 2θ values being ±0.2.

The XRPD pattern of the form A of mesylate for nicotinamide derivative mesylate in the present invention is shown in FIG. 1.

In the present invention, the form A of mesylate for nicotinamide derivatives contains 2.5 to 4.5% (w/w) waters, and it is preferable that the form A of mesylate for nicotinamide derivatives is a monohydrate compound.

The present invention also provides a method for preparing form A of mesylate for nicotinamide derivatives, which comprises the following steps: feeding nicotinamide derivatives mesylate into an organic solvent, the ratio of the nicotinamide derivatives mesylate to the organic solvent is 1:150-250 g/ml, preferably the ratio is 1:200 g/ml, slurring in the shaker at a temperature between room temperature to 35° C., then filtering and drying under vacuum to get a white powder as form A of mesylate for nicotinamide derivatives, preferably, the form A of mesylate for nicotinamide derivatives is monohydrate.

In the method above, the organic solvent is any one of alcohols, ethers, esters, ketones, aliphatic hydrocarbons and aromatic hydrocarbon organic solvents, or a mixture of any two or more thereof by any ratio.

In the method above, the alcoholic organic solvent is methanol, ethanol, isopropanol, n-propanol, isobutanol, n-butanol or a mixture of any two or more thereof by any ratio;
the ethereal organic solvent is isopropyl ether or methyl-tert-butyl ether;
the ester organic solvent is ethyl acetate or butyl acetate;
the ketone organic solvent is butanone or 4-methyl-2-pentanone;
the aliphatic hydrocarbon organic solvent is n-heptane;
the aromatic hydrocarbon organic solvent is toluene.

The present invention also provides a method for preparing form A of mesylate for nicotinamide derivatives, which comprises the following steps: dissolving the nicotinamide derivatives mesylate in methanol, the ratio of the nicotinamide derivatives mesylate to the methanol is 1:25-35 g/ml, preferably the ratio is 1:30 g/ml, and then dropwise adding isopropyl ether, methyl-tert-butyl ether or acetonitrile, the dropwise adding of the isopropyl ether, methyl-tert-butyl ether or acetonitrile is stopped when there are solid precipitates, leaving standstill the above reaction suspension liquid until an off-white solid is obtained, and filtering and drying under vacuum to get a white powder as the form A of mesylate for nicotinamide derivatives, preferably, the form A of mesylate for nicotinamide derivatives is monohydrate.

The present invention also provides a method for preparing the form A of mesylate for nicotinamide derivatives, which comprises the following steps: dissolving mesylate of the nicotinamide derivatives in dimethylformamide, the ratio of the mesylate of the nicotinamide derivatives to the dimethylformamide is 1:35-50 g/ml, preferably the ratio is 1:40 g/ml and then dropwise adding isopropyl ether, methyl-tert-butyl ether or acetonitrile, the dropwise adding of the isopropyl ether, methyl-tert-butyl ether or acetonitrile is stopped when there are solid precipitates, leaving standstill the above reaction suspension liquid until an off-white solid is obtained, filtering the off-white solid, and drying under vacuum to get a white powder as the form A of mesylate for nicotinamide derivatives, preferably, the form A of mesylate for nicotinamide derivatives is monohydrate.

Those skilled in the art will be able to adjust the amounts of reagents used for the method of the present invention based on their knowledge and experience, including scaling up or down the amount of the feedstock used and adjusting the amount of the solvent used, which are also included in the method of the present invention.

The present invention also provides a new crystal form-form A, for the above nicotinamide derivatives mesylate, more particularly, an application of the form A of mesylate for nicotinamide derivatives for treating advanced non-small cell lung cancer, gastric cancer, liver cancer or breast cancer.

The form A of mesylate for nicotinamide derivatives more particularly, an application of the form A of mesylate for nicotinamide derivatives provided by the present invention has excellent high-temperature stability, high-humidity stability and illumination stability, it is advantageous for pharmaceutical processing and pharmaceutical compositions, and it can be applied to drugs for treating advanced non-small cell lung cancers, gastric cancers, liver cancer or breast cancer. It has preferable bioavailability, and meanwhile the provided qualitative and quantitative information has great significance on further study of the efficacy of such solid drugs.

DETAILED DESCRIPTION OF THE INVENTION

Figure 1:
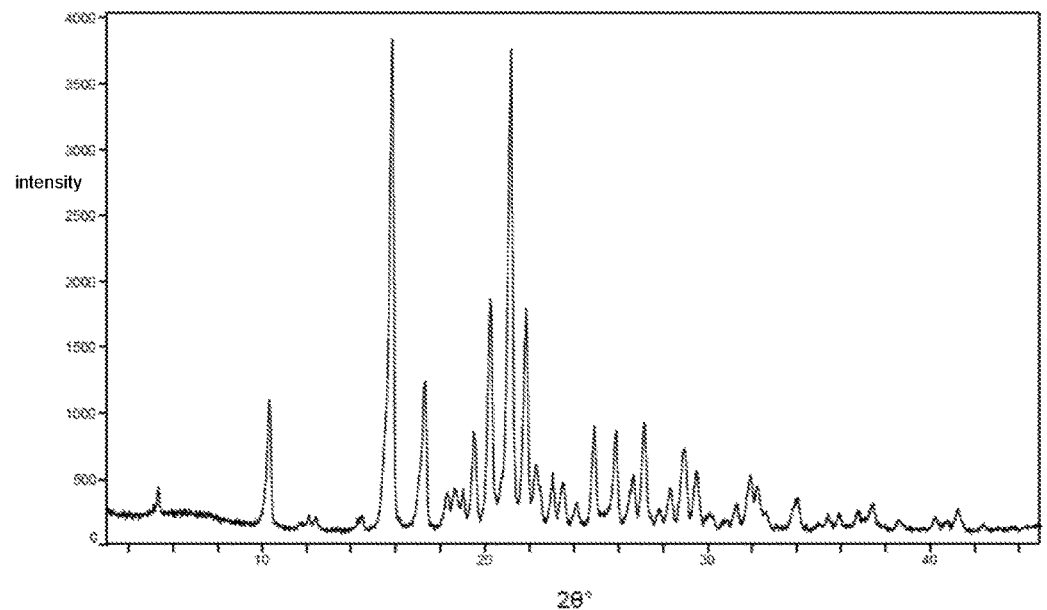
FIG. 1 is the XRPD pattern of the form A of mesylate for nicotinamide derivatives provided by the present invention.

The invention will hereafter be described in detail with reference to the appended drawings.

Embodiment 1. Preparation of the Form A of Mesylate for Nicotinamide Derivatives the Present Invention 1 g of nicotinamide derivatives mesylate was dissolved in 200 ml of organic solvent, slurried in a shaker at room temperature for 48 hours, then filtered, dried under vacuum to obtain a white powder as the form A of mesylate for niacinamide derivatives.

The organic solvent used may be any one of the following types of organic solvents, or a mixture of any two or more of the following types of organic solvents by any ratio:
alcoholic organic solvent includes: methanol, ethanol, n-propanol, isopropanol, n-butanol, isobutanol and the like.

Ethereal organic solvent includes: isopropyl ether and methyl-tert-butyl ether.

The ester organic solvent includes: ethyl acetate and butyl acetate.

The ketone organic solvent includes: butanone and 4-methyl-2-pentanone.

The aliphatic hydrocarbon organic solvent includes: n-heptane.

The aromatic hydrocarbon organic solvent includes: toluene.

An automatic moisture instrument was adopted for detection, and the moisture content of the obtained product was 2.71%.

Embodiment 2. Preparation of the Form A of Mesylate for Niacinamide Derivatives in the Present Invention 500 mg of the mesylate of the nicotinamide derivatives was fed into 75 ml of organic solvent, shaken in a shaker at a temperature of 35° C. for 48 hours, then filtered, and dried under vacuum to obtain a white powder as the form A of mesylate for niacinamide derivatives mesylate.

The organic solvent used may be any one of the following types of organic solvents, or a mixture of any two or more of the following types of organic solvents by any ratio:
alcoholic organic solvent includes: methanol, ethanol, n-propanol, isopropanol, n-butanol, isobutanol and the like.

Ethereal organic solvent includes: isopropyl ether and methyl-tert-butyl ether.

The ester organic solvent includes: ethyl acetate and butyl acetate.

The ketone organic solvent includes: butanone and 4-methyl-2-pentanone.

The aliphatic hydrocarbon organic solvent includes: n-heptane.

The aromatic hydrocarbon organic solvent includes: toluene.

An automatic moisture instrument was adopted for detection, and the moisture content of the obtained product was 3.43%.

Embodiment 3. Preparation of the Form A of Mesylate for Niacinamide Derivatives in the Present Invention 2 g of the mesylate of the nicotinamide derivatives was fed into a 500 ml of organic solvent, shaken in a shaker at room temperature for 48 hours, then filtered, and dried under vacuum to obtain a white powder as the form A of mesylate for niacinamide derivatives.

The organic solvent used may be any one of the following types of organic solvents, or a mixture of any two or more of the following types of organic solvents by any ratio:
alcoholic organic solvent includes: methanol, ethanol, n-propanol, isopropanol, n-butanol, isobutanol and the like.

Ethereal organic solvent includes: isopropyl ether and methyl-tert-butyl ether.

The ester organic solvent includes: ethyl acetate and butyl acetate.

The ketone organic solvent includes: butanone and 4-methyl-2-pentanone.

The aliphatic hydrocarbon organic solvent includes: n-heptane.

The aromatic hydrocarbon organic solvent includes: toluene.

An automatic moisture instrument was adopted for detection, and the moisture content of the obtained product was 2.98%.

Embodiment 4. Preparation of the Form A of Mesylate for Niacinamide Derivatives in the Present Invention 500 mg of the mesylate of nicotinamide derivatives was dissolved in 15 mL of the methanol (AR), and then the isopropyl ether (AR) was dropwise added, the adding of the isopropyl ether (about 8 ml) was stopped when there were solid precipitates, the reaction solution was left standstill at room temperature for 12 hours to obtain an off-white color solid which was filtered, and dried under vacuum to obtain a 200 mg of white powder (the yield was 40%) as the form A of mesylate for niacinamide derivatives.

An automatic moisture instrument was adopted for detection, and the moisture content of the obtained product was 3.52%.

Embodiment 5. Preparation of the Form A of Mesylate for Niacinamide Derivatives in the Present Invention 1 g of the mesylate of nicotinamide derivatives was dissolved in 25 mL of methanol (AR), and then the methyl tert-butyl ether (AR) was dropwise added, the adding of the methyl tert-butyl ether (about 56 ml) was stopped when there were solid precipitates, the reaction solution was left standstill at room temperature for 12 hours to obtain an off-white color solid which was filtered, and dried under vacuum to obtain a 502 mg of white powder (the yield was 50%) as the form A of mesylate for niacinamide derivatives.

An automatic moisture instrument was adopted for detection, and the moisture content of the obtained product was 4.21%.

Embodiment 6. Preparation of the Form A of Mesylate for Niacinamide Derivatives in the Present Invention 1.5 g of the mesylate of nicotinamide derivatives was dissolved in 53 mL of the methanol (AR), and then the acetonitrile (AR) was dropwise added, the adding of the acetonitrile (about 24 ml) was stopped when there were solid precipitates, the reaction solution was left standstill at room temperature for 12 hours to obtain an off-white color solid which was filtered, and dried under vacuum to obtain a 690 mg of white powder (the yield was 46%) as the niacinamide derivatives mesylate of Form A.

An automatic moisture instrument was adopted for detection, and the moisture content of the obtained product was 2.5%.

Embodiment 7. Preparation of the Form A of Mesylate for Niacinamide Derivatives in the Present Invention 500 mg of the mesylate of nicotinamide derivatives was dissolved in 20 mL of the dimethylformamide (AR), and then the isopropyl ether (AR) was dropwise added, the adding of the isopropyl ether (about 48 ml) was stopped when there were solid precipitates, the reaction solution was left standstill at room temperature for 12 hours to obtain an off-white color solid which was filtered, and dried under vacuum to obtain a 190 mg of white powder (the yield was 38%) as the form A of mesylate for niacinamide derivatives.

An automatic moisture instrument was adopted for detection, and the moisture content of the obtained product was 3.23%.

Embodiment 8. Preparation of the Form A of Mesylate for Niacinamide Derivatives in the Present Invention 5 g of the mesylate of nicotinamide derivatives was dissolved in 250 mL of dimethylformamide (AR), and then methyl tert-butyl ether (AR) was dropwise added, the adding of the methyl tert-butyl ether (about 480 ml) was stopped when there were solid precipitates, the reaction solution was left standstill at room temperature for 12 hours to obtain an off-white color solid which was filtered, and dried under vacuum to obtain a white powder of 2.3 g (the yield was 46%) as the form A of mesylate for niacinamide derivatives.

An automatic moisture instrument was adopted for detection, and the moisture content of the obtained product was 4.5%.

Embodiment 9. Preparation of the Form A of Mesylate for Niacinamide Derivatives in the Present Invention 1 g of the mesylate of nicotinamide derivatives was dissolved in 35 mL of dimethylformamide (AR), and then acetonitrile (AR) was dropwise added, the adding of the acetonitrile (about 96 ml) was stopped when there were solid precipitates, the reaction solution was left standstill at room temperature for 12 hours to obtain an off-white color solid which was filtered, and dried under vacuum to obtain a white powder of 421 mg (the yield was 42%) as the form A of mesylate for niacinamide derivatives.

An automatic moisture instrument was adopted for detection, and the moisture content of the obtained product was 3.5%.

In conclusion, the automatic moisture instrument was adopted to detect multiple copies of the mesylate crystal form A of nicotinamide derivatives prepared by adopting the method of the present invention, and its moisture content was 2.5~4.5%.

Embodiment 10. Preparation of the Contrast Needles Shape Solid of Nicotinamide Derivatives Mesylate According to the preparation method disclosed in a Chinese patent CN101676267, 500 mg of the mesylate of nicotinamide derivatives is dissolved in 7 mL of 95% isopropanol water solution, the mixture was performed nitrogen protection, stirring and heating under the dark condition to realize complete dissolution, and it was filtered while it was still hot, filtrate was cooled and crystallized to room temperature, then filtered and washed with isopropanol, and dried under vacuum to obtain 315 mg of white needle-like crystals (the yield was 63%) as the needles solid of the nicotinamide derivatives mesylate.

Figure 2:
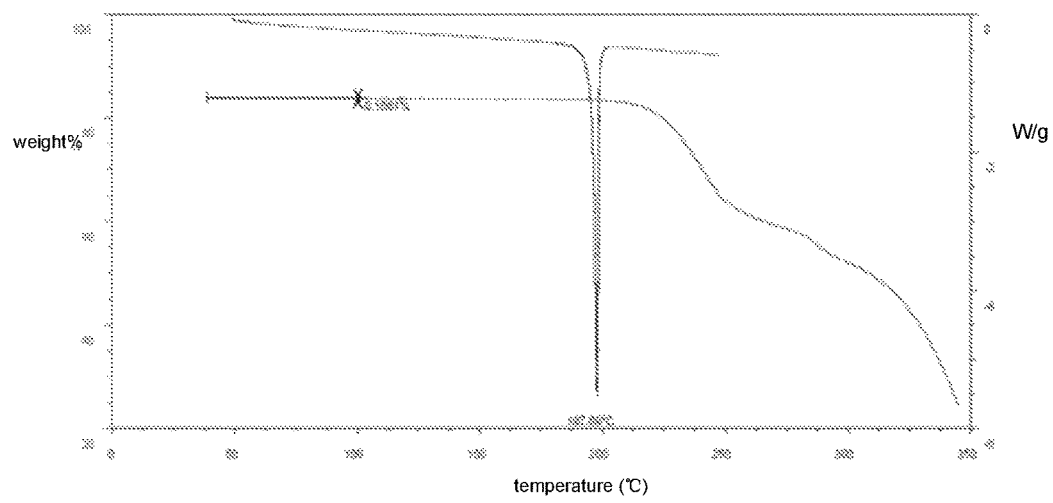
FIG. 2 is the DSC-TGA pattern of contrastive needle solid of the form A of mesylate for nicotinamide derivatives.
Figure 3:
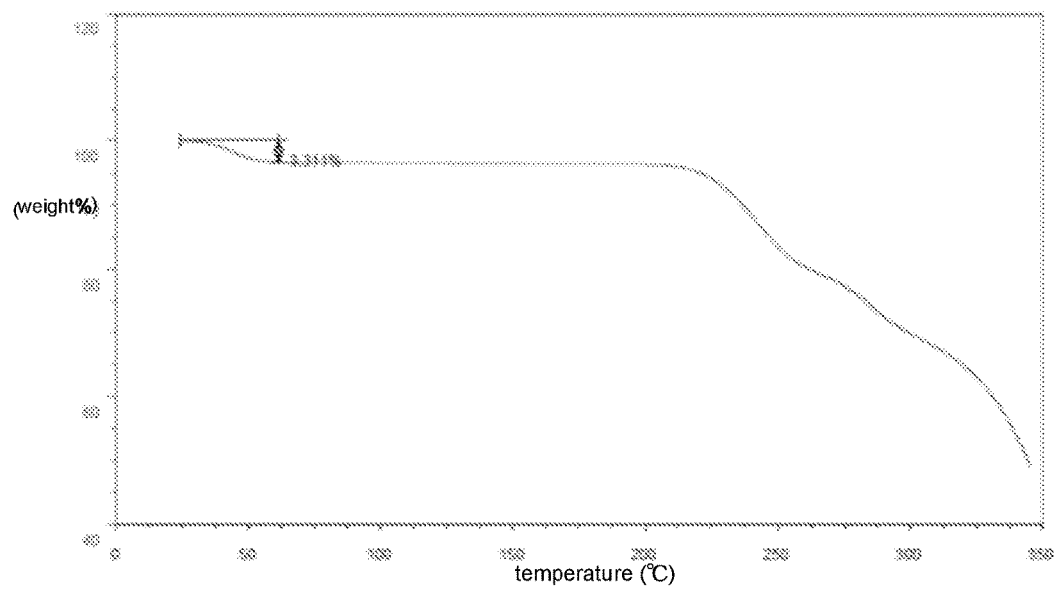
FIG. 3 is the TGA pattern of the contrast needle shape solid of the nicotinamide derivatives mesylate under the humidity condition for 24 hours.
Figure 4:
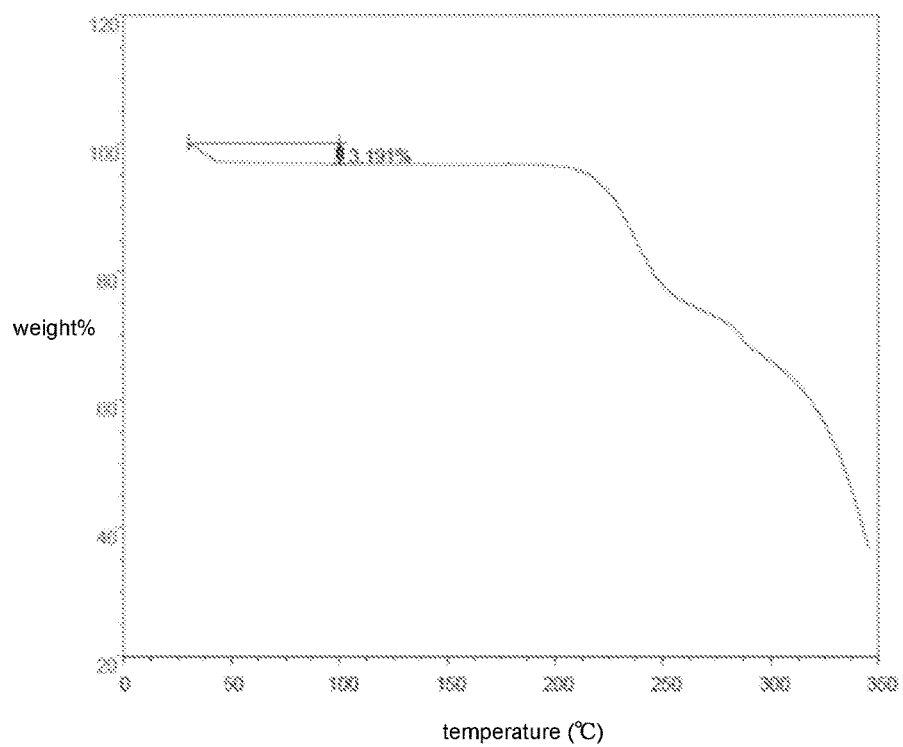
FIG. 4 is the TGA pattern of the contrast needle shape solid of the nicotinamide derivatives mesylate under the humidity condition for 48 hours.
Figure 5:
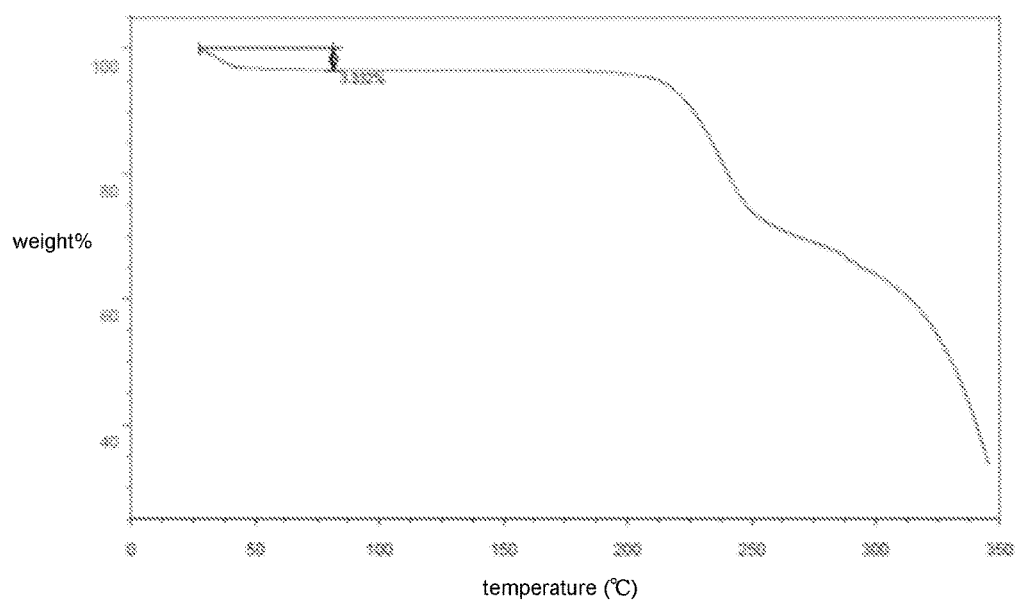
FIG. 5 is the TGA pattern of the contrast needle shape solid of the nicotinamide derivatives mesylate under the humidity condition for 72 hours.

Embodiment 11. Hygroscopicity Determination of the Contrast Needles Shape Solid of Nicotinamide Derivatives Mesylate The obtained compound referred in a Chinese patent CN101676267 was 180.2 g of white needle-like crystals (0.365 mol) with the molecular weight being 493.5. It can thus be seen that the contrast needles shape solid of nicotinamide derivatives mesylate was anhydrate. The white needles of nicotinamide derivatives mesylate were prepared according to the method of embodiment 8, and a DSC-TGA pattern of the needles as shown in FIG. 2 was obtained. Wherein, the testing conditions of differential scanning calorimetry (DSC) were 10° C./min with range of 30-300° C., and TGA testing conditions were 10° C./min from room temperature to 350° C. A proper amount of the needle samples of nicotinamide derivatives mesylate were placed at the room temperature under the humidity condition of 40%, and TGA detection was conducted on the solid respectively at the time intervals of 24 hours, 48 hours and 72 hours. After the samples were placed at the room temperature for 24 hours, as shown in FIG. 3, the TGA pattern of the contrast needles showed that the weight loss was 3.311%; after the samples were placed at the room temperature for 48 hours, as shown in FIG. 4, the TGA pattern of the contrast needles showed that the weight loss was 3.191%; after the samples were placed at the room temperature for 72 hours, as shown in FIG. 5, the TGA pattern of the contrast needles showed that the weight loss was 3.332%. It can thus be seen that the contrast needles had a certain hygroscopicity.

Embodiment 12. Characterization of the Form A of Mesylate for Niacinamide Derivatives in the Present Invention Through an XRPD Pattern The details of XRPD instrument/collected information were as follows:
CuK$_\alpha$ radiation (tube operating at 40 KV and 40 mA), and combined multifunctional X-ray diffractometer of Rigaku Ultima IV model were configured and used to obtain an X-ray powder diffraction (XRPD) pattern. Data were obtained by using a scanning speed of 20°/min, a scanning step length was 0.02, a slit width of 0.01 and a 2θ range of a scanning range of 3-45°. A glass slide was adopted to directly perform pressing on a testing plate for sample processing.

The XRPD (X-ray powder diffraction) pattern of the form A of mesylate for niacinamide derivatives prepared according to the method of the embodiment 4 was as shown in FIG. 1, and specific representations were as follows:

| 2θ | d | I % |
| --- | --- | --- |
| 5.34 | 16.5367 | 5.2 |
| 10.341 | 8.5472 | 28.5 |
| 11.764 | 7.5164 | 2.9 |
| 12.04 | 7.3446 | 3.9 |
| 12.405 | 7.1292 | 4 |
| 14.438 | 6.1298 | 4.3 |
| 15.841 | 5.5899 | 100 |
| 17.32 | 5.1158 | 33.5 |
| 18.301 | 4.8438 | 9.1 |
| 18.68 | 4.7463 | 8.9 |
| 19.005 | 4.6658 | 5.6 |
| 19.577 | 4.5307 | 21.8 |
| 20.26 | 4.3796 | 51.9 |
| 21.161 | 4.1951 | 98.1 |
| 21.859 | 4.0627 | 44.6 |
| 22.379 | 3.9695 | 14.1 |
| 23.04 | 3.8569 | 11.4 |
| 23.5 | 3.7825 | 14.1 |
| 24.177 | 3.6782 | 6.5 |
| 24.959 | 3.5646 | 22.9 |
| 25.881 | 3.4397 | 22.3 |
| 26.641 | 3.3432 | 12.3 |
| 27.18 | 3.2781 | 28.7 |
| 27.802 | 3.2063 | 3.4 |
| 28.3 | 3.1509 | 8.6 |
| 28.999 | 3.0766 | 18.7 |
| 29.501 | 3.0254 | 15.5 |
| 30.065 | 2.9698 | 3 |
| 31.279 | 2.8573 | 5.4 |
| 31.96 | 2.7979 | 12.3 |
| 32.258 | 2.7728 | 12.1 |
| 33.999 | 2.6347 | 8 |
| 35.451 | 2.53 | 3.2 |
| 35.941 | 2.4967 | 3.1 |
| 36.798 | 2.4404 | 3.2 |
| 37.38 | 2.4038 | 5.8 |
| 38.657 | 2.3273 | 3 |
| 40.245 | 2.239 | 3.5 |
| 40.822 | 2.2087 | 3.4 |
| 41.297 | 2.1844 | 6.9 | d represents an interplanar distance of two adjacent crystal faces in crystal lattices with angstrom as the unit, and I % represents intensity.

The XRPD (X-ray powder diffraction) patterns of the form A of mesylate for niacinamide derivatives prepared according to the methods of the embodiment 1-3 and the embodiment 5-9 are substantially the same as the pattern as shown in FIG. 1.

It can be seen from FIG. 1 that the XRPD pattern of the form A of mesylate for niacinamide derivatives provided by the present invention has diffraction peaks at 2θ values of 5.34, 10.341, 14.438, 15.841, 17.32, 18.301, 18.68, 19.005, 19.577, 20.26, 21.161, 21.859, 22.379, 23.04, 23.5, 24.177, 24.959, 25.881, 26.641, 27.18, 28.3, 28.999, 29.501, 31.96, 32.258, 33.999, 36.798, 37.38 and 41.297 with the error range of 2θ values being ±0.2.

The error range of the 2θ values also can be ±0.15 through testing. It should be understood by the field technicians that theses diffraction peaks do not represent the details about the diffraction peaks shown by the form A of mesylate for niacinamide derivatives. The 2θ values of the X-ray powder diffraction pattern can slightly change with machines and changes and batch changes in sample preparation, and referenced values are not regarded as absolute values. It should be also understood that the relative intensity of the peaks possibly changes with the orientation effect, therefore the intensity shown in XRD path lines contained in the present invention is exemplary but is not used for absolute comparison.

Embodiment 13. Characterization of the Form A of Mesylate for Niacinamide Derivatives the Present Invention Through DSC-TGA DSC-TGA testing conditions are 10° C./min from room temperature to 350° C.

Figure 6:
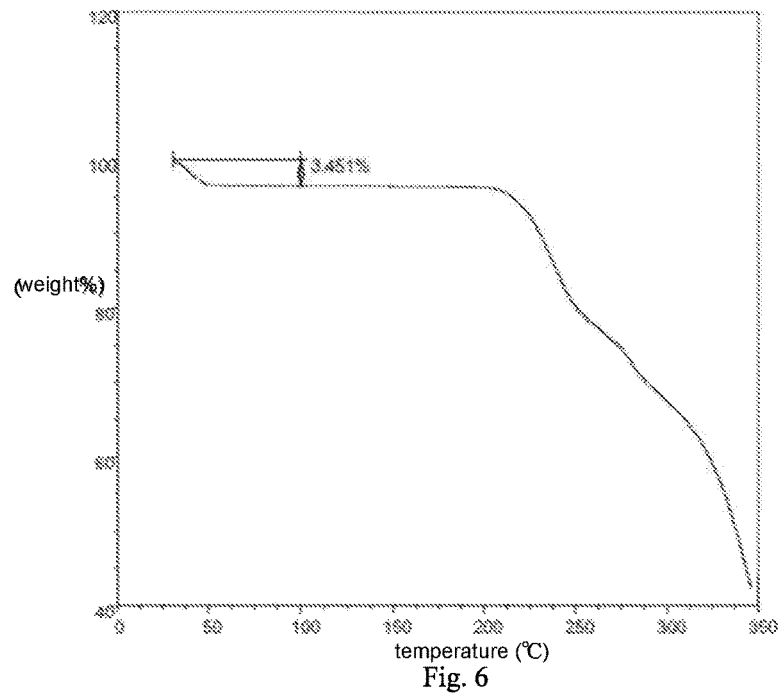
FIG. 6 is the TGA pattern of form A of mesylate for nicotinamide derivatives provided by the present invention.

The mesylate crystal form A of nicotinamide derivatives prepared according to the method of the embodiment 4 shows one dehydrating peak at the temperature of 72~75° C. and one heat-absorbing fusion peak at a temperature of 198~200° C. As shown in FIG. 6, a proper amount of the mesylate crystal form a sample of nicotinamide derivatives is placed for TGA detection, and it shown that the weight loss is 3.451%. The TGA pattern of the crystal form A and the above-mentioned moisture testing result indicate that the crystal form A is mesylate monohydrate.

The DSC-TGA pattern of the mesylate crystal form A of nicotinamide derivatives prepared according to the method of the embodiment 9 is substantially the same as the pattern of the example 4.

Embodiment 14. Determination of High-Temperature Stability, High-Humidity Stability and Light Stability of the Mesylate Crystal Form A of Nicotinamide Derivatives of the Present Invention The mesylate crystal form A of nicotinamide derivatives prepared according to the method of the embodiment 4 was tested.

(1) High-Temperature Stability

Figure 7:
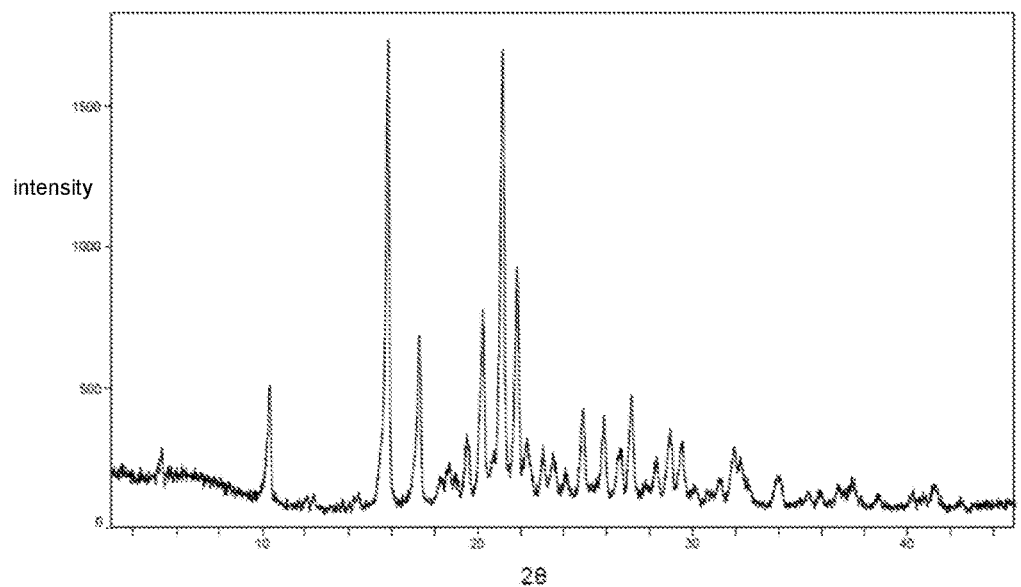
FIG. 7 is the XRPD pattern showing a high-temperature stability test of the form A of mesylate for nicotinamide derivatives provided by the present invention.

The mesylate crystal form A sample of nicotinamide derivatives was placed in an airtight drying oven of 60° C. and then was taken out after 5 days for XRPD testing, the XRPD pattern was as shown in FIG. 7, and the comparison result of the FIG. 1 and FIG. 7 indicated that the form A of mesylate for niacinamide derivatives had good high-temperature stability.

(2) High-Humidity Stability

Figure 8:
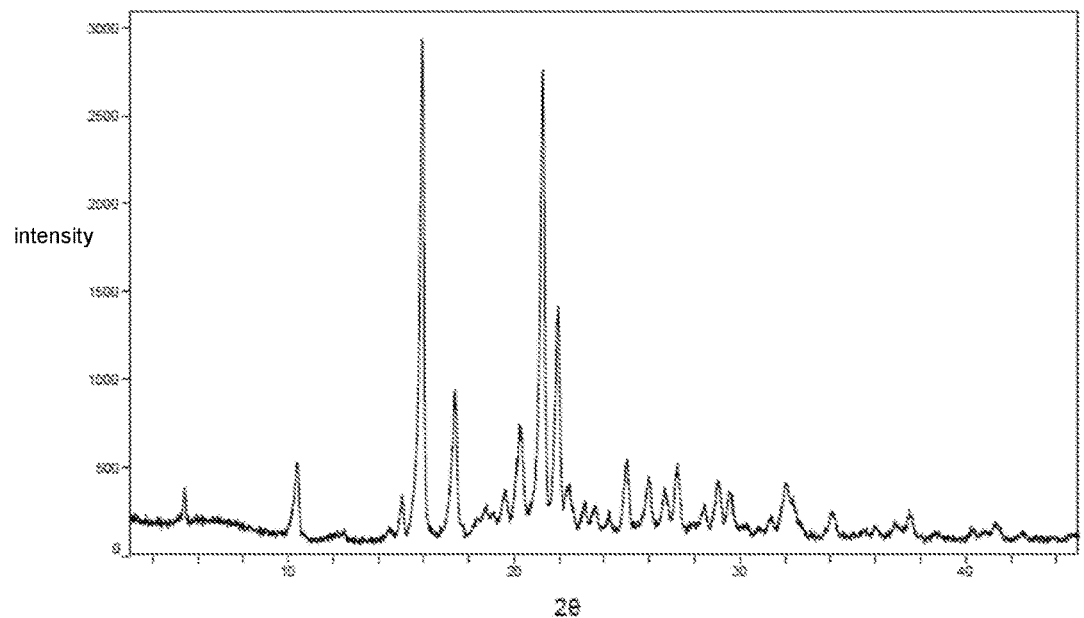
FIG. 8 is the XRPD pattern showing a high-humidity stability test of the form A of mesylate for nicotinamide derivatives provided by the present invention.

The mesylate crystal form A sample of nicotinamide derivatives was placed in an airtight container with the humidity condition of 92.5% and then was taken out after 5 days for XRPD testing, the XRPD pattern was as shown in FIG. 8, and the comparison result of the FIG. 1 and FIG. 8 indicated that the mesylate crystal form A of nicotinamide derivatives had good stability in a high-humidity environment.

(3) Light Stability

Figure 9:
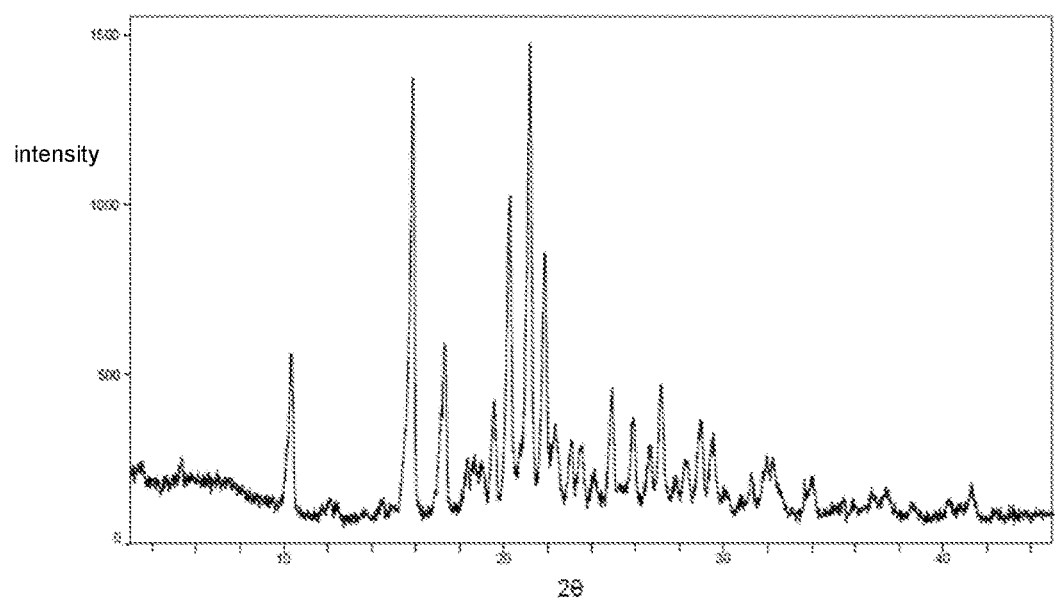
FIG. 9 is the XRPD pattern showing the photostability of the form A of mesylate for nicotinamide derivatives provided by the present invention.

The form A of mesylate for niacinamide derivatives was placed in a transparent container and subjected to light with the intensity of 4500 lux and then was taken out after 5 days for XRPD testing, the XRPD pattern was as shown in FIG. 9, and the comparison result of the FIG. 1 and FIG. 9 indicated that the form A of mesylate for niacinamide derivatives had good light stability.

Embodiment 15. Solubility Comparison of Different Crystal Forms

The form A of mesylate for niacinamide derivatives prepared according to the method of the embodiment 4 and the needle solid of nicotinamide derivatives mesylate prepared according to the method of the embodiment 10 were respectively dissolved in water and ethanol, and solubility results were shown in Table 1.

TABLE 1

Solubility comparison results of different crystal forms

| Inspection conditions | The form A of mesylate for niacinamide derivatives of the present invention | Contrast needles |
|---|---|---|
| Water solubility | Insoluble | Insoluble |
| Ethanol solubility | 0.1 g/18 ml | 0.1 g/20 ml |

It can be seen from the above results that the mesylate crystal form A of nicotinamide derivatives of the present invention has better solubility than the contrast needles.

Embodiment 16. Stability Comparison of Different Crystal Forms Determined by HPLC The form A of mesylate for niacinamide derivatives prepared according to the method of the embodiment 4 and the mesylate needles of nicotinamide derivatives prepared according to the method of the embodiment 10 were respectively put in the environment with light, high humidity (relative humidity (RH) is 90%), room temperature and high temperature (60° C.) for 6 months, the contents of related substances of the sample were determined by adopting HPLC, and examination results were shown in Table 2. HPLC testing conditions: chromatographic column Venusil MP-C18 (4.6 mm×250 mm, 5 μm, 100 Å); Mobile phase A: 0.1% acetum, B: acetonitrile, gradient conditions (0 min, 95% A; 20 min, 5% A; 25 min, 5% A; 30 min, 95% A); Detection wavelength 254 nm; Flowing speed 1 ml/min; Column temperature 30° C.; Sample amount 20 μl.

TABLE 2

Stability comparison results of different crystal forms determined by adopting HPLC

| Inspection conditions | The form A of mesylate for niacinamide derivatives of the present invention | Contrast needles |
|---|---|---|
| Illuminating for 6 months | 99.6% | 99.4% |
| RH90% for 6 months | 98.5% | 98.8% |
| Room temperature for 6 months | 99.4% | 99.2% |
| 60° C. for 6 months | 98.1% | 98.2% |

It can be seen from the above results that the chemical properties of both the mesylate crystal form A of nicotinamide derivatives of the present invention and the contrast needles are very stable.

Embodiment 17. Stability Comparison of Different Crystal Forms Determined by Adopting Solid-State Representation Means The form A of mesylate for niacinamide derivatives prepared according to the method of the embodiment 4 and the needles solid of nicotinamide derivatives mesylate prepared according to the method of the embodiment 10 were respectively put in the environment with light, high humidity (relative humidity (RH) is 90%), room temperature and high temperature (60° C.) for 6 months, XRPD determination was performed by adopting a solid-state representation means, and examination results were shown in Table 3.

TABLE 3

Stability comparison results of different crystal forms determined by adopting solid-state representation means

| Inspection conditions | The form A of mesylate for niacinamide derivatives of the present invention | Contrast needles |
|---|---|---|
| Illuminating for 6 months | Unchanged | Unchanged |
| RH90% for 6 months | Unchanged | The crystal form A of the present invention |
| Room temperature for 6 months | Unchanged | The crystal form A of the present invention |
| 60° C. for 6 months | Unchanged | Unchanged |

It can be seen from the above results that the form A of mesylate for niacinamide derivatives in the present invention is more stable than needles in chemical property and the needles can be converted into the more stable crystal form A under the humidity condition.

The form A of mesylate for niacinamide derivatives provided by the present invention can be applied to drugs for the treatment of advanced non-small cell lung cancers, gastric cancers, liver cancers or breast cancers, and meanwhile the provided qualitative and quantitative information has the important significance on further study of the efficacy of such solid drugs.

The present invention is not limited to the above best implementation modes, and it should be known that any structural change is employed under the inspiration of the present invention, and any technical solution same as or similar to the present invention falls into the scope claimed by the present invention.

What is claimed is:

1. A form A of mesylate for nicotinamide wherein the XRPD pattern has a diffraction peak at 2θ values of 5.34, 10.341, 14.438, 15.841, 17.32, 18.301, 18.68, 19.005, 19.577, 20.26, 21.161, 21.859, 22.379, 23.04, 23.5, 24.177, 24.959, 25.881, 26.641, 27.18, 28.3, 28.999, 29.501, 31.96, 32.258, 33.999, 36.798, 37.38 and 41.297 with the error range of the 2θ values being ±0.2.

2. The form A of mesylate for nicotinamide according to claim 1, wherein the XRPD pattern thereof is shown in FIG. 1.

3. The form A of mesylate for nicotinamide according to claim 1, wherein the form A of mesylate for nicotinamide has a water content of from 2.5 to 4.5%, and the mesylate A of the nicotinamide is a monohydrate mesylate of the nicotinamide.

4. A method for preparing the form A of mesylate for nicotinamide according to claim 3, further comprising the following steps: feeding a mesylate of a nicotinamide derivative into an organic solvent, the ratio of the mesylate of nicotinamide to organic solvent is 1:150~250 g/ml, and the ratio is 1:200 g/ml, shaking in a shaker at room temperature, then filtering and drying under vacuum to get a white powder as the form A of mesylate for nicotinamide.

5. The method according to claim 4, wherein the organic solvent is any one of alcohols, ethers, esters, ketones, aliphatic hydrocarbons and aromatic hydrocarbon organic solvents, or a mixture of any two or more thereof by any ratio.

6. The method according to claim 5, wherein,
the alcoholic organic solvent is methanol, ethanol, isopropanol, n-propanol, isobutanol, n-butanol or;
the ethereal organic solvent is isopropyl ether or methyl-tert-butyl ether;
the ester organic solvent is ethyl acetate or butyl acetate;
the ketone organic solvent is butanone or 4-methyl-2-pentanone;
the aliphatic hydrocarbon organic solvent is n-heptane;
the aromatic hydrocarbon organic solvent is toluene.

7. A method for preparing the form A of mesylate for nicotinamide according to claim 3, further comprising the following steps: dissolving a mesylate of nicotinamide in methanol, the ratio of the mesylate of nicotinamide to the methanol is 1:25~35 g/ml, and the ratio is 1:30 g/ml, and then dropwise adding isopropyl ether, methyl-tert-butyl ether or acetonitrile, the dropwise adding of the isopropyl ether, methyl-tert-butyl ether or acetonitrile is stopped when there are solid precipitates, leaving standstill the above reaction liquid until an off-white solid is obtained, filtering the off-white solid, and drying under vacuum to get a white powder as the form A of mesylate for nicotinamide.

8. A method for preparing the form A of mesylate for nicotinamide according to claim 3, further comprising the following steps: dissolving a mesylate of nicotinamide in dimethylformamide, the ratio of the mesylate of nicotinamide to the dimethylformamide is 1:35~50 g/ml, and the ratio is 1:40 g/ml, and then dropwise adding the isopropyl ether, methyl-tert-butyl ether or acetonitrile, the dropwise adding of the isopropyl ether, methyl-tert-butyl ether or acetonitrile is stopped when there are solid precipitates, leaving standstill the above reaction liquid until an off-white solid is obtained, filtering the off-white solid, drying under vacuum to get a white powder as the form A of mesylate for nicotinamide.

9. A method of cancer treatment comprising administering the form A of mesylate for nicotinamide of claim 1 to a patient wherein cancer is treated by blocking endothelial growth factor tyrosine kinase dependent new blood vessel formation in tumor tissue.

10. The form A of mesylate for nicotinamide according to claim 2, wherein the form A of mesylate for nicotinamide has a water content of from 2.5 to 4.5%, and the mesylate A of the nicotinamide is a monohydrate mesylate of the nicotinamide.

11. A method for preparing the form A of mesylate for nicotinamide according to claim 10, further comprising the following steps: feeding a mesylate of a nicotinamide derivative into an organic solvent, the ratio of the mesylate of nicotinamide to the organic solvent is 1:150~250 g/ml, and the ratio is 1:200 g/ml, shaking in a shaker at room temperature, then filtering and drying under vacuum to get a white powder as the form A of mesylate for nicotinamide.

12. The method according to claim 11, wherein the organic solvent is any one of alcohols, ethers, esters, ketones, aliphatic hydrocarbons and aromatic hydrocarbon organic solvents, or a mixture of any two or more thereof by any ratio.

13. A method of cancer treatment comprising administering the form A of mesylate for nicotinamide of claim 2 to a patient wherein cancer is treated by blocking endothelial growth factor tyrosine kinase dependent new blood vessel formation in tumor tissue.

14. A method of cancer treatment comprising administering the form A of mesylate for nicotinamide of claim 3 to a patient wherein cancer is treated by blocking endothelial growth factor tyrosine kinase dependent new blood vessel formation in tumor tissue.

15. A method of cancer treatment comprising administering the form A of mesylate for nicotinamide of claim 10 to a patient wherein cancer is treated by blocking endothelial growth factor tyrosine kinase dependent new blood vessel formation in tumor tissue.

* * * * *